United States Patent [19]

Marino

[11] Patent Number: 4,981,653
[45] Date of Patent: Jan. 1, 1991

[54] SELF-INDICATING STRIP

[75] Inventor: Rebecca A. Marino, Elkhart, Ind.

[73] Assignee: Miles Inc., Elkhart, Ind.

[21] Appl. No.: 254,165

[22] Filed: Oct. 6, 1988

[51] Int. Cl.$^5$ ............................................. G01N 31/00
[52] U.S. Cl. ...................................... 422/56; 422/57; 422/58; 436/810; 435/804
[58] Field of Search ..................... 422/55, 61, 56, 57, 422/58, 69; 436/8, 66, 164, 169, 810; 435/4, 805, 292

[56] References Cited

U.S. PATENT DOCUMENTS

| | | | |
|---|---|---|---|
| 2,981,606 | 4/1961 | Keston | 422/56 |
| 3,964,871 | 6/1976 | Hochstrasser | 435/805 |
| 4,046,514 | 9/1977 | Johnston et al. | 436/71 |
| 4,175,923 | 11/1979 | Friend | 422/56 |
| 4,683,209 | 7/1987 | Ismail et al. | 436/8 |
| 4,734,360 | 3/1988 | Phillips | 435/805 |

FOREIGN PATENT DOCUMENTS 8301308  4/1983  World Int. Prop. O. ............ 422/57

Primary Examiner—Robert A. Wax
Assistant Examiner—William H. Beisner
Attorney, Agent, or Firm—Roger N. Coe

[57] ABSTRACT

The present invention relates generally to an analytical reagent test strip for assaying fluid samples. The reagent test strip of this invention has a self-indicating format which provides accurate and reliable results without the need for a color chart or instrument analysis. In the preferred embodiment of this invention, reagent threads are incorporated into and protrude through a polymer housing. The threads are placed in a particular pattern whereby different colored configurations will occur in response to different concentrations of analyte in a sample. The present invention is accurate, reliable and convenient to use.

9 Claims, 5 Drawing Sheets

SELF-INDICATING STRIP

BACKGROUND OF THE INVENTION

1. Field of the Invention

The present invention relates generally to analytical reagent test strips for assaying fluid samples. More specifically, the reagent test strip of this invention is directed to a self-indicating format which provides accurate and reliable visual results without the need for an instrument or color chart.

2. Discussion of the Prior Art

Reagent test strips in general have been known for some time and are widely used in the health care industry. Such devices are called test "strips," because they typically comprise long, narrow sections of plastic or paper used both as a handle and as a support for a carrier matrix located at one end. The carrier matrix is generally a small paper-like pad which is incorporated with a reagent system.

When using a reagent test strip, the matrix is usually contacted with an analytical sample. The matrix is typically designed to take up the analytical sample by capillary action, and the sample thereby contacts and interacts with the reagent system of the matrix. The reagent system is typically designed to provide a color response in proportion to the amount of a particular analyte in the sample.

To determine the test strip's color change, the strip is generally either placed in an instrument, such as a reflectance photometer, or is compared with a color chart. However, instruments which read color are often expensive, may have reliability problems, and may require complex maintenance and operation by a skilled technician.

Color charts may fade due to sunlight or other ambient conditions or perhaps just due to time. Color charts may be expensive to manufacture and may be inconvenient for an operator to handle, particularly if the reagent strip and the color chart are to be handled together. Furthermore, persons with color perception problems may not be able to interpret a color chart properly. Moreover, a color chart standardized in a laboratory may not be accurate in the field where nonlaboratory conditions might alter test strip's color change, providing a color change that would not occur under laboratory conditions.

U.S. Pat. No. 4,042,329 by Hochstrasser is directed to a device for detecting cholesterol having a self-indicating format. In Hochstrasser, different reagent systems are incorporated into different "zones" of a bibulous, absorbent support material, such as paper. However, keeping each reagent separate during the incorporation process can be difficult, because as each reagent system moves into the absorbent carrier, it will continue to migrate throughout the carrier until it "dries", i.e., until substantially all of the solvent evaporates out of the reagent solution. In such a system, drying is a function of time, temperature, convection currents, substrate composition, solution composition and solution volume. With so many parameters to control, such a method for reagent incorporation is prone to error. Furthermore, once the support is wetted with a sample, the reagent systems will once again be able to migrate and perhaps interact with one another. Hochstrasser suggests adding a nonabsorbent cover to the carrier with appropriately spaced apertures, thereby hiding areas between the reagent systems from a user of the system; this may cover up and help reduce the adverse effect of the migration problem, but certainly does not solve it. Also, applying different reagent systems to discrete zones of a support is a complex task that is not well suited for large scale manufacturing.

U.S. Pat. No. 4,046,514 to Johnston et al. is directed to a reagent strip with a self-indicating format. However, the Johnston device requires an interweaving of reagent threads and also requires that the resulting woven material be affixed to a support. However, weaving reagent threads is a complex process and affixing woven material to a support member can also be a cumbersome process which is not well suited to large scale manufacturing. The reagents in the interwoven threads can be prone to interact with one another, perhaps causing unwanted side reactions. Also, the adhesive which adheres the woven threads to the support adds to the system's complexity and may not be reliable or may interfere with the system.

Consequently, it is an object of the present invention to provide a self-indicating reagent test strip which is reliable, easy to manufacture, and can be accurately read by persons without the need for special technical skill or training and without the need for an analytical instrument or color chart.

A further object of the present invention is to provide a reagent test strip which will provide an accurate reading notwithstanding adverse environmental influences.

Other objects and features of the present invention will become apparent to those skilled in the art after reviewing the following specification.

SUMMARY OF THE INVENTION

The present invention relates generally to an analytical reagent test strip for assaying fluid samples. The reagent test strip of this invention has a self-indicating format which provides accurate and reliable results without the need for a color chart or instrument analysis. In the preferred embodiment of this invention, reagent threads are incorporated into and protrude through a polymer housing. The threads are placed in a particular pattern whereby different colored configurations will occur in response to different concentrations of analyte in a sample. The present invention is accurate, reliable and convenient to use.

DETAILED DESCRIPTION OF THE PREFERRED EMBODIMENT

Figure 1:
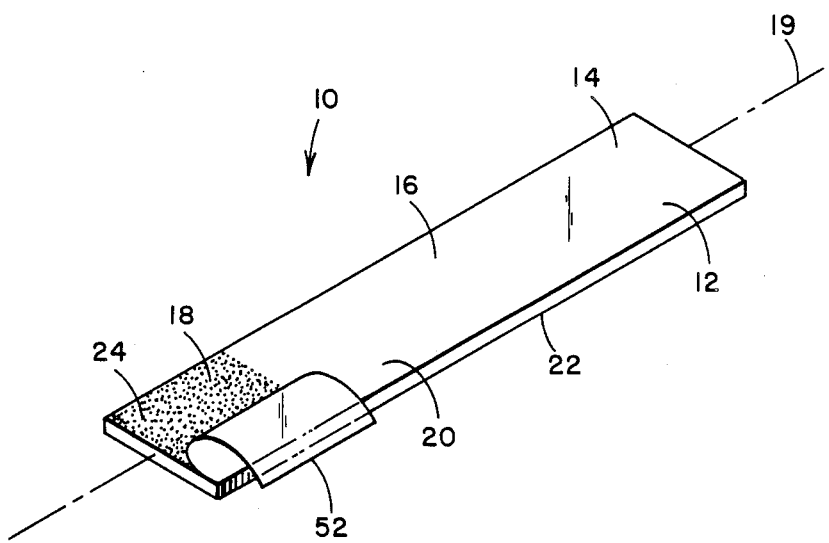
FIG. 1 is a perspective view of the preferred embodiment of this invention.

The preferred embodiment of the present invention is shown generally at 10 in FIG. 1, and comprises a rectangular polymer housing 12 defining a rearward, middle and forward portion (illustrated at 14, 16, and 18 respectively) along a central axis 19 and further defining a top and bottom side, the top side illustrated at 20 and the bottom side illustrated at 22. The rearward portion 14 provides a handle for grasping, preferably along the top and bottom sides, to physically manipulate the device.

The forward portion 18 of housing 12 encases reagent threads 24. These threads are oriented perpendicular to the central axis and perpendicular to the top and bottom sides of housing 12. As shown in FIG. 1, the reagent threads protrude through the housing and are exposed at the top and the bottom of the housing.

The reagent threads of this invention can comprise natural or synthetic fibers, spun glass, plastic micro tubes filled with a gelatin reagent system, and the like. Examples of natural fibers would include cotton, wool, and cellulose. Examples of synthetic fibers would include nylon, polypropylene, polyurethane, and the like. In selecting the composition of the reagent threads, special care should be taken to ensure that the threads retain the reagent system and still have the capability of taking up and retaining a sufficient amount of sample. The threads should not interfere with the chemical reactions used to determine the analyte of interest. Moreover, the threads should also not interfere with the user's ability to read the resulting response once a sample is contacted with the threads. The reagent threads need not be absorbent in cases such as where the reagent system is coated along the outside of the thread. Indeed if the coating itself is absorbent, pulling the sample into the reagent system, the reagent thread would not need to be absorbent and would merely act as a support.

In use, a sample is placed upon the top side of the forward portion of the housing, whereby the sample contacts the reagent threads and is absorbed into the threads by capillary action. The sample contacts the analytical reagents incorporated within each thread. The analyte of interest within the sample will react with these reagents in a predictable manner to create a detectable, analytical response in proportion to the concentration of analyte within the sample.

Reagent systems for assaying samples are known generally in the art, and need not be discussed in detail here. The present invention is not directed to any particular reagent system, but rather is directed to an innovative means for supporting one or more reagent systems.

Each reagent thread in the preferred embodiment can be incorporated with a different reagent system or different versions of the same reagent system. In this way, each thread can provide a meaningful test result. A user can read these results together and thereby obtain more information than if the device only contained one reagent system.

The present invention is readily adaptable to narrowly defined assay systems, such as systems which provide a single color response under a very precise condition, i.e., a particular analyte concentration. Different threads can then be incorporated with different assay systems, and the totality of threads can thereby provide an extremely precise assay response.

Figure 2:
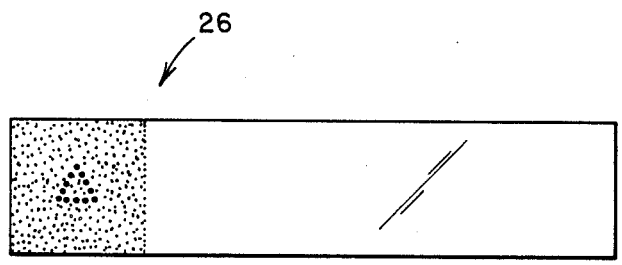
FIGS. 2–4 are top views of an alternative embodiment of this invention, each showing a possible assay response.
Figure 3:
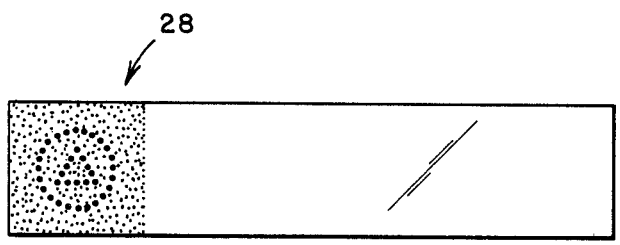
Figure 4:
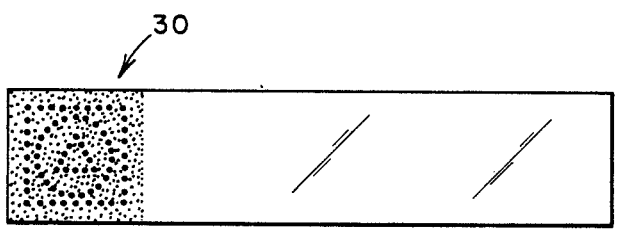

The reagent threads incorporated with a particular assay system can be placed in a particular pattern within the polymer housing. An assay system which turns from clear to blue in the presence of 100 mg glucose per deciliter sample can be incorporated into a number of threads and placed in a triangular configuration within the housing as shown generally at 26 in FIG. 2, and an assay system which provides a similar response but in the presence of 200 mg/dL (glucose concentration) could be placed in a circular configuration surrounding this triangle as shown generally at 28 in FIG. 3, and yet a third assay system providing a similar response but in the presence of 300 mg/dL (glucose concentration) could be placed in a square configuration enclosing the previous two configurations, as shown generally at 30 in FIG. 4.

In determining glucose concentrations in samples, such a system would show a blue triangle in the presence of 100 mg/dL, a blue triangle enclosed by a blue circle in the presence of 200 mg/dL, and a blue square enclosing the triangle and circle in the presence of 300 mg glucose per deciliter of sample. Such a system would eliminate the need to distinguish different shades of a particular color, such as in many conventional reagent strip systems. The test strip of this invention is easily and accurately read without the need for a color chart comparison.

Furthermore, such a system can be viewed more favorably by the public than conventional color chart systems. In comparing shades of colors to a color chart, consumers can be skeptical of their ability to accurately interpret the color shade and can also be skeptical that the test is sufficiently accurate to truly create different shades of color in response to analyte concentration. In the present invention, colored configurations may have considerable market appeal, since consumers may perceive the difference between a circle and triangle to be more accurate than the difference between certain shades of color.

Furthermore, if a conventional strip provides no response, the consumer may wonder whether the result is due to the lack of the analyte of interest or whether it is due to a defect in the strip. In the present invention, since numerous reagent systems can be incorporated into the strip, a "self-test" can be incorporated into the system to ensure the accuracy of the system, and to encourage confidence in the analytical result. For example, referring back to the example described above, a user who sees a triangle, then a circle and then a square may have more confidence in the assay system than the consumer who merely sees a strip turn a particular color and then change to a different shade of color.

Figure 5:
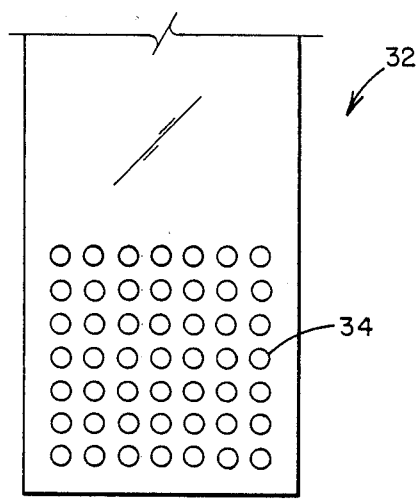
FIGS. 5–8 are top views of another alternative embodiment, each showing a possible assay response.
Figure 6:
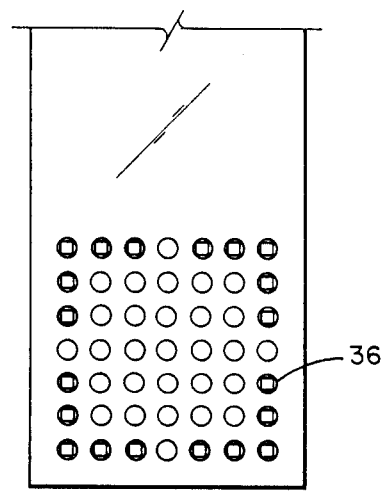
Figure 7:
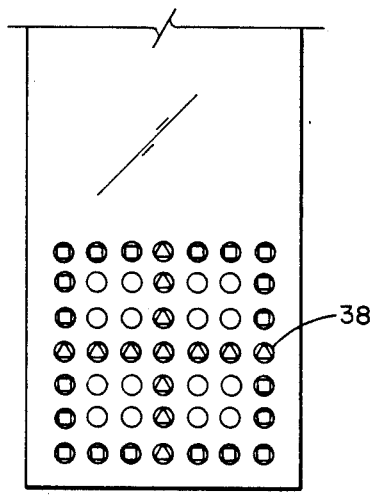
Figure 8:
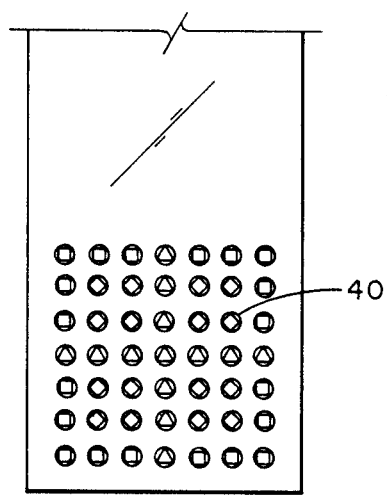

In another embodiment of this invention a ten by ten square configuration of reagent threads can be incorporated with a reagent system as shown generally at 32 in FIG. 5, which will turn yellow upon the application of a sample having no glucose. Such yellow threads are indicated by the circles 34 in FIG. 5. The threads along the outer perimeter could then be treated with an additional reagent system to turn red in the presence of 500 mg of glucose per deciliter of sample. Such red threads are indicated by circles 36 encompassing squares in FIG. 6. Reagent threads defining a horizontal and vertical line crossing at the center of the square configuration could be incorporated with a reagent system which would turn blue in the presence of a 1000 mg/dL (glucose concentration) and such blue threads are shown in FIG. 7 as circles 38 encompassing triangles. Finally, the remaining threads within the outer perimeter (but not including the crossing vertical and horizontal lines) could be incorporated with a reagent system which would turn green in the presence of 2000 mg glucose dL of sample as shown in FIG. 8 as circles 40 encompassing diamonds. Such a self-indicating reagent strip system is easy to use and interpret.

Figure 9:
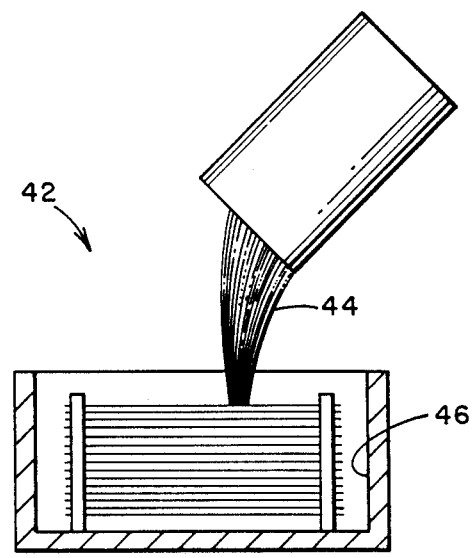

Once an appropriate thread is chosen, a reagent system can typically be incorporated within the thread by moving the thread through a reagent dip solution. After drawing the threads through the solution, the threads can be held in a particular spatial relationship parallel to one another by a mechanical means such as is shown generally at 42 in FIG. 9. After "threading" the mechanical means, a substance such as liquid TRYCITE ®, gelatin, or synthetic polymer, shown generally at 44 in FIG. 9, can be poured into a mold 46 surrounding the mechanical means and allowed to solidify.

Figure 10:
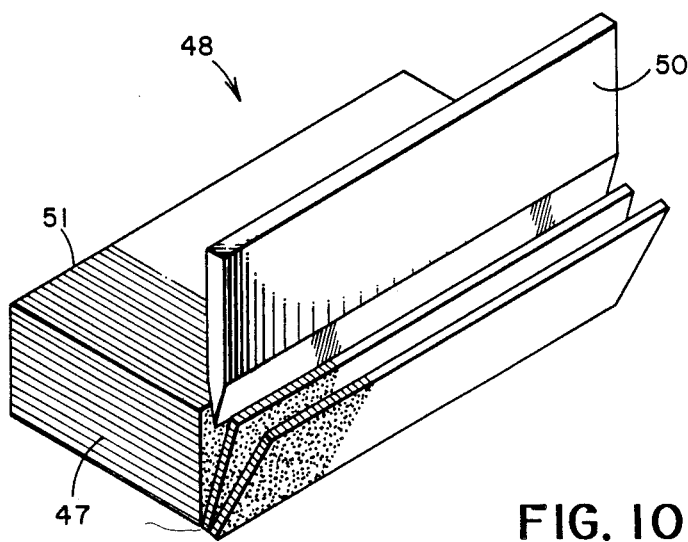
FIGS. 9–10 illustrate a preferred method of manufacturing the present invention.

The resulting solid block 47 shown in FIG. 10 can then be sliced perpendicular to the reagent threads 51 as shown generally in FIG. 10 at 48 by cutting means 50, thereby creating strips such as the strip 10 illustrated in FIG. 1, having reagent threads protruding perpendicular to the top and bottom planes of the strip. Since the thread pattern protrudes through both sides of the strip, a sample can be placed on either side or both. If a thread composition is chosen which takes up sample into only a relatively small portion of the thread, then a separate test could be conducted with each side (top and bottom) of the reagent strip. Hence a standard solution could be placed on one side of the reagent threads, a sample placed on the opposite side, and the results compared.

The present invention can be designed to have significant structural integrity. Unlike many conventional strips having reagent pads which can be knocked off or otherwise separated from their support, the present system comprises reagent threads which are firmly embedded within a support housing; this support housing can be made of a sturdy material, such as TRYCITE ®, and the reagent threads can be made of a sturdy, tightly woven synthetic or natural fiber. Such a sturdy system can withstand rigorous treatment, such as where mechanical stress is placed on the system, i.e. when a sample must be blotted or wiped off subsequent to application to the strip.

Therefore, aside from the self-indicating, easy-to-read nature of this invention, this system can also be advantageously used in applications resulting in relatively high mechanical stress. Therefore the design requirements for a machine or instrument to manipulate the reagent strip of this invention would not necessarily require gentle mechanical treatment as is typical in conventional reagent pad strip systems.

A protective adhesive strip, such as the one shown at 52 in FIG. 1, can be placed over the reagent threads to protect the reagent threads from ambient conditions until just prior to use. Such an adhesive strip could be reliably removed due to the high degree of structural integrity possible for this invention.

The reagent threads can be design to have particular physical properties such as relatively small sample size take up. Such threads could be used with assay reagent systems which do not require a large sample to provide a sufficient detectable response. This may be quite advantageous for persons who are inconvenienced by the relatively large sample size required by many reagent pad systems, such as persons who must prick their fingers for a blood sample. Indeed, this assay system may allow for a much smaller lancing means for collecting a blood sample which may reduce the discomfort to the patient.

Also, without a cumbersome pad protruding from the support, the present system will typically be easy to package and easy for a user to physically manipulate relative to many conventional reagent pad systems.

Since the threads preferably protrude through the support, the operator has the option of applying a sample to either the top or bottom side.

Figure 11:
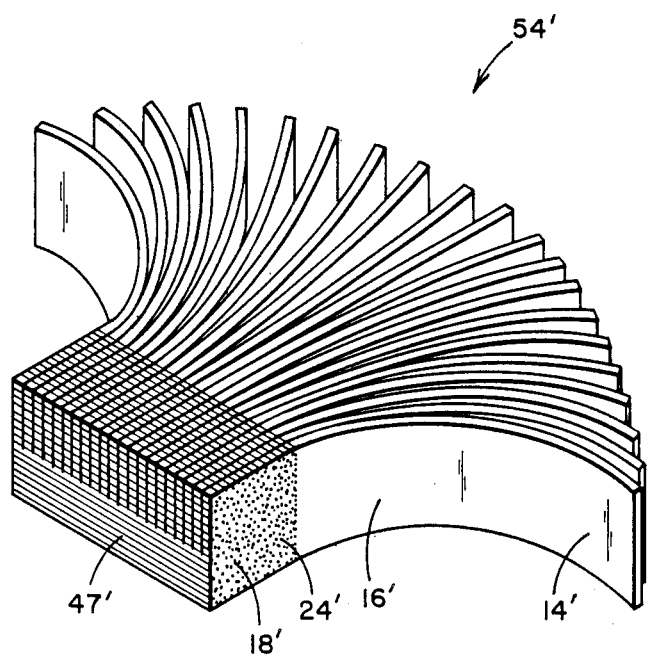
FIG. 11 is a perspective view of an alternative embodiment of the present invention

An alternative embodiment of this invention, as illustrated generally at 54' in FIG. 11, relates to a semi-rigid housing embedded with reagent threads which easily break apart. In such a system, the housing is molded around the reagent threads as discussed above, but instead of cutting the resulting block 47' into strips as described above, the block is only partially cut along its forward and middle portions (shown at 14' and 16' respectfully).

Thereafter, the end user can grab onto forward portion 14' and pry or tear the rearward portion 18' away from this block 47', thereby providing a reagent strip ready for use. According to this design, the reagent threads 24' will break at the point where the top portion separates from the block. In such a system reagent threads comprising gelatin are preferred, although other designs are certainly possible.

One advantage to the alternative embodiment of FIG. 11 is that the portion of the reagent threads exposed due to the above described prying action will not be exposed to air, sunlight, humidity, etc., until the strip is pried away from the block 47'. Such a system would be most advantageous for reagent systems which have stability problems, since outside interferences can be minimized until just prior to use. Another advantage of this alternative embodiment would be reduced cost to the customer, since each strip does not have to be packaged individually.

An apparatus could be used to separate strips from block 47'. Such a system would be especially advantageous in a hospital type environment since a nurse or similar type personnel could quickly and easily grab the dispensing device, pull the trigger or equivalent activation means and have a strip protrude from the device which could be contacted with a sample. The user could read the result quickly and easily, because the reagent strip of this invention can be designed to provide a quick and easy reading as already discussed.

After reading the result, further manipulation of the device, such as a further pulling of the trigger, could dispel the strip into a disposal container. Such a system would be very convenient for medical personnel, diminishing their possible exposure to samples, such as blood or urine. The device would also be simple to use, since a cartridge comprising block 47' would be loaded into the device, thereby providing the device with numerous reagent strips to be dispensed. The device could be designed such that the reagent threads would not be exposed to ambient conditions until the trigger (or equivalent) is activated as discussed above, and therefore, the reagent threads could be protected from ambient conditions until just prior to use.

In yet another embodiment of the invention, certain threads would not be incorporated with reagent, but rather, would be incorporated with a stable, inert ink. Different inks could be used for different threads to provide varying colors which would preferably correlate with the entire range of possible reagent thread color changes.

Alternatively, the "ink" within the ink threads could merely be a particular reagent system reacted with a known amount of analyte; as such, a very precise color standard can be incorporated into the strip. By using a reagent system rather than a conventional ink, any color change error by the reagent system would affect the "color standard" thread and reagent thread equally. The color change error of the reagent thread will parallel the color change error of the ink thread, thereby diminishing the potential color error of the test. A conventional color chart is incapable of accounting for such color errors.

The ink threads could be interspersed with the reagent threads. Each ink color could be a particular standard and could be identified by its position on the reagent strip or by a symbol placed on the strip.

The ink threads could provide a color chart useful in reading the reagent thread color change. This embodiment has substantial advantages over conventional color charts which are separate from a reagent strip. First, the user will not have to go looking for the color chart once a reading is to be taken, since the color chart in essence is incorporated into the strip. Second, the ink thread can be placed very close to the reagent thread, thereby allowing for a more accurate color comparison.

Alternatively, the ink threads could be used to create a permanent pattern within the strip to provide information to the user. The ink threads would be more durable than merely printing the pattern onto the strip and may be cheaper to incorporate into the strip than conventional printing techniques. The ink threads could form a trademark or identify and distinguish the strip from other reagent strips. Alternatively, the ink threads could be incorporated within the strip to provide instructions or merely for aesthetic purposes.

The present invention is defined by the claims which are provided below, and the present discussion is merely provided to help understand the claims and understand the numerous possible embodiments of the present invention as defined by the claims. The limitations defining this invention are expressly outlined in the claims, and nothing provided in this discussion is intended to provide any additional limitations thereto.

What is claimed is:

1. A self indicating assay device, said device comprising:
   a support having top and bottom surfaces,
   a first reagent thread substantially encased within said support perpendicular to said surfaces and partially exposed at at least one of said surfaces of said support,
   said first reagent thread comprising a material incorporated with a first reagent system, whereby a sample placed upon the exposed portion of said thread will come in contact with said first reagent system thereby causing a visual response which can be observed by viewing at least one of said surfaces of said device.

2. The self-indicating assay device of claim 1 further comprising a second reagent thread partially encased within said support and partially exposed at one of said surfaces of said support, wherein said second reagent thread comprises a material incorporated with a second reagent system, said second reagent system providing a visual response to a fluid sample different from the response provided by said first reagent system.

3. The self-indicating assay device of claim 2 further comprising a third reagent thread partially encased within said support and partially exposed at one of said surfaces of said support, wherein said third reagent thread comprises a stable colored substance to be used as a color standard against which the color change in said first or second reagent system can be compared.

4. The self-indicating assay device of claim 3 wherein the stable colored substance is further defined by a reagent system which has been reacted with a known amount of analyte.

5. The self-indicating assay device of claim 4 wherein said first, second and third threads are substantially parallel to one another.

6. A self indicating assay device, said device comprising:
   an elongated support having top and bottom surfaces,
   a first reagent thread and a second reagent thread, each of which is partially encased within said support perpendicular to said surfaces and partially exposed at least one of said surfaces of said support,
   said first and second reagent threads comprising an absorbent material wherein the absorbent material in the first thread is incorporated with a first reagent system and the absorbent material in the second thread is incorporated with a second reagent system, whereby said absorbent material will readily take up a fluid sample placed it in contact with said reagent systems thereby causing a visual response which can be observed by viewing one of said surfaces of said device.

7. The self indicating assay device of claim 6 further defining a protective covering over said reagent threads which can be peeled away prior to use.

8. A self indicating assay device, said device comprising:
   a support strip defining a top surface and a bottom surface, said surfaces being substantially parallel to one another,
   a first set of reagent threads and a second set of reagent threads, each set of said reagent threads being partially encased within said support and exposed at the top and bottom surfaces of said support, wherein each reagent thread is substantially perpendicular to the top and bottom surfaces of said support strip,
   said first and second set of reagent threads comprising an absorbent material whereby the absorbent material in the first set of threads is incorporated with a first reagent system and the absorbent material in the second set of threads is incorporated with a second reagent system,
   whereby said absorbent materials will readily take up a fluid sample placing it in contact with said reagent systems, thereby causing a visual response in proportion to the amount of analyte in said sample, said response being observable when viewing at least one of said surfaces of said support.

9. A method of manufacturing a self-indicating reagent strip, said method comprising:
   incorporating a plurality of parallel threads containing one or more reagent system in a mold whereby said threads are retained substantially parallel to one another,
   pouring a solidifying agent into said mold thereby encasing said threads,
   allowing said solidifying agent to solidify,
   removing the resulting solidified material from said mold, and
   slicing said solidified material in a manner whereby said reagent threads are perpendicular to and are exposed at one or more primary surfaces of said solidified agent.

* * * * *